United States Patent [19]

Whellock et al.

[11] Patent Number: 5,021,069

[45] Date of Patent: Jun. 4, 1991

[54] METHOD OF EFFECTING A BIOREACTION

[76] Inventors: John G. Whellock, 9400 East Iliff Avenue, #134, Denver, Colo. 80231; Jonathan Goodbody, 45A Elsworthy Road, London NW3 3BS, England

[21] Appl. No.: 286,944

[22] Filed: Dec. 20, 1988

[30] Foreign Application Priority Data

Oct. 6, 1988 [GB] United Kingdom ............... 8823533

[51] Int. Cl.$^5$ ..................... C10L 9/10; C22B 3/00; C12S 13/00
[52] U.S. Cl. .................................. 44/622; 435/282; 423/DIG. 17
[58] Field of Search ............... 44/622, 625; 435/262, 435/282; 75/6, 9

[56] References Cited

U.S. PATENT DOCUMENTS 4,206,288  6/1980  Detz et al. ........................ 44/625
4,497,778  2/1985  Pooley ............................... 75/6

FOREIGN PATENT DOCUMENTS 1596738  8/1981  United Kingdom .
2177618  1/1987  United Kingdom .

Primary Examiner—Carl F. Dees
Attorney, Agent, or Firm—Watson, Cole, Grindle & Watson

[57] ABSTRACT

A bioreaction is affected by oxygenating a liquid/solids mixture containing a micro-organism to enable the bioreaction to proceed, wherein the said mixture is confined in a reaction vessel and circulated around a loop, the loop including a column in which gas transfer is effected, at least the liquid being introduced into the top of the column in the form of at least one stream, the velocity of which stream is sufficient to generate and maintain, at least in an upper region of the column, a substantially continuous foam formed of close-packed bubbles of the gas in the liquid extending across the entire cross-section of the column, driven to violent agitation and backmixing by the incoming stream of liquid, and of relatively uniform bubble size, the velocity of the inlet stream of liquid and the rate of introduction of the gas being sufficient to prevent gas accumulating at the top of the column.

20 Claims, 5 Drawing Sheets

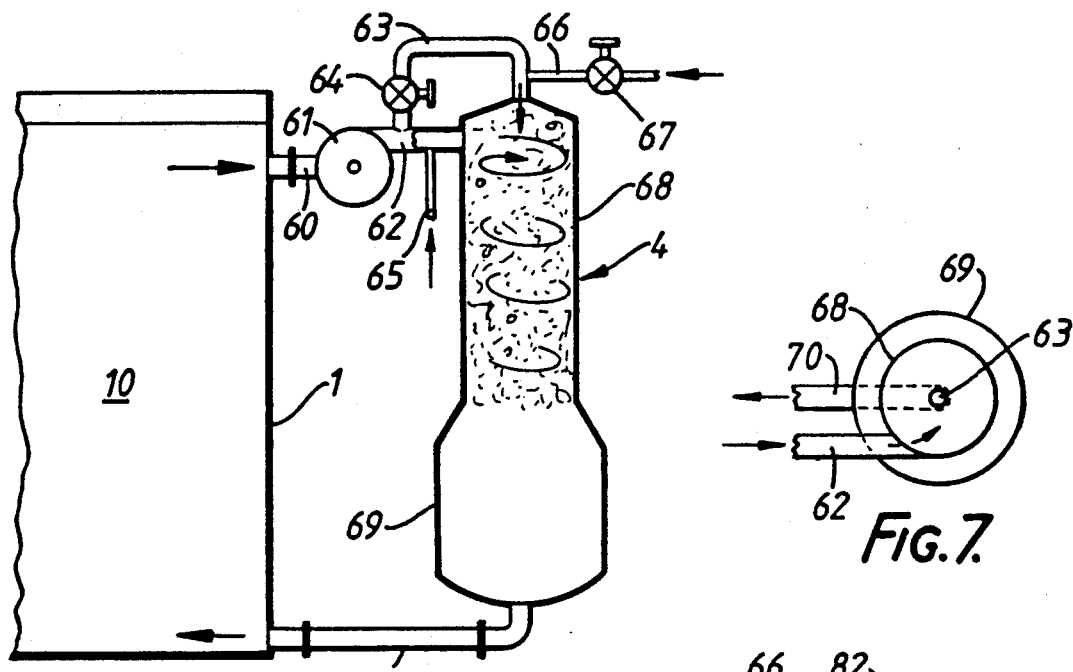
Fig. 6.
Fig. 7.
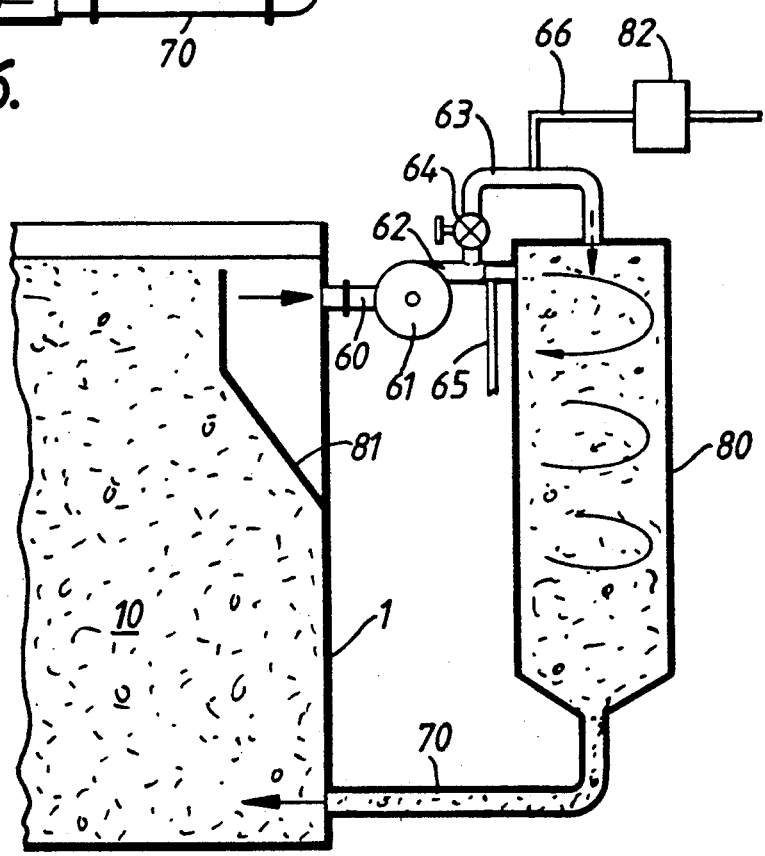
Fig. 8.

METHOD OF EFFECTING A BIOREACTION

This invention relates to a method of effecting a bioreaction involving solids, liquid and gas.

In the chemical, pharmaceutical and mineral industries, there are often requirements for contacting gases, liquids and solids simultaneously. A typical requirement is for carrying out a bioreaction where there is a need to supply air or oxygen to a reacting biomass in conjunction with a solid phase. Such gas/liquid/solid contacting usually involves the use of significant amounts of energy to bring the phases in contact and to generate interfacial area of the air or oxidant in the form of bubbles. In a fermentor, for example, a specially designed agitator with provision for air or oxygen injection is often used. In the mineral industry, where it is desired, for example, to leach or react a sulfide-containing ore with oxygen through the agency of an aerobic biomass, other methods have been used such as elastomeric diaphragms or porous plate distributors in conjunction with an agitator or stirrer to achieve the transfer of air or oxygen into the liquid phase. Once in solution, the biomass makes use of the oxygen in effecting the necessary metallurgical reaction or oxidation. In either of the above systems or methods, the demands for air/oxygen transfer are substantial, especially where the solids concentration in the reactor is large, such as 20 to 30 percent w/w. In such case, there is extreme difficulty in transferring the desired quantities of gas without substantial energy expenditures for agitation or gas compression. In other instances, the transfer of oxygen or air may be restricted due to the low interfacial area presented between the gas and the liquid phase. To overcome these limitations, a higher driving force for oxygen transfer is necessary but this leads to as little as 15 percent of the available oxygen being applied to the process. Frequently, the operating economics hinge on the efficiency of transfer of oxygen, whether from an oxygen or an air supply.

The problems of providing an adequate transfer of oxygen to a large-scale biomass reaction are not only economic problems. It is also generally recognised in the art that care must be taken to avoid subjecting the biomass to any severe turbulence or shear, since this can severely damage the micro-organisms and slow down or even kill the process. It has been common practice, therefore, to supply oxygen (or air) through submerged spargers or bubble diffusers and to provide only relatively gentle, non-damaging stirring to the biomass.

We have now found that, very surprisingly, at least some bioreactions can be carried out with greatly improved efficiency utilising an oxygenation process which involves subjecting the biomass to considerable turbulence and shear. The oxygenation process itself has substantially higher efficiency than is obtainable conventionally and also gives rise to further advantages in the bioreaction process itself.

According to one aspect of the present invention, there is provided a method of effecting a bioreaction which comprises oxygenating a liquid/solids mixture containing a micro-organism to enable the bioreaction to proceed, which comprises confining the said mixture in a reaction vessel and circulating the mixture around a loop, the loop including a column in which gas transfer is effected, at least the liquid being introduced into the top of the column in the form of at least one stream, the velocity of which stream(s) is sufficient to generate and maintain at least in an upper region of the column, a substantially continuous foam formed of close-packed bubbles of the gas in the liquid extending across the entire cross-section of the column, driven to violent agitation and backmixing by the incoming stream(s) of liquid, and of relatively uniform bubble size, the velocity of the inlet stream(s) of liquid and the rate of introduction of the gas being sufficient to prevent gas accumulating at the top of the column.

Gas-transfer in a column is described in U.K. patent no. 1596738, whose teachings are incorporated herein by reference, and to which reference should be made for further details. The process essentially involves forming a continuous highly agitated turbulent foam of the liquid/solids biomass reaction mixture in the column. Within the foam, the bubbles move in all directions and the phenomena of dispersion, dissolution and coalescence occur simultaneously and continuously. As a result, there is a highly efficient transfer of oxygen into the liquid/solids mixture, which is ideal for the purposes of the bioreaction.

U.K. patent specification no. 2177618A describes a further column gas-transfer process in which a combination of rotary and vertical circulatory motion about and along the vertical axis of the column is used. This technique can also be used in the present invention, and the teachings of the said U.K. specification 2177618A are incorporated herein by reference. This technique is particularly useful where pure oxygen (as opposed to air) is used.

These column techniques for introducing gas into a liquid (or liquid/solids mixture) involve subjecting the liquid to fierce turbulence and shear. Hitherto, such conditions have been carefully avoided by those practising bioreactions, because these conditions can damage biomass particularly in the case of micro-organisms which require careful handling. However, we have found that, overall, at least some bioreactions are not at all deleteriously affected but rather are very considerably enhanced. The enhancement derives not merely from the greatly improved oxygen transfer which the column technique provides, but also from the turbulence and shear themselves. Thus, for example, we have found that one effect of the turbulence and shear is to break down any clumps in the biomass, thus increasing the exposed surface area and also apparently lowering the viscosity of the mixture, both of which features are advantageous. Other advantages will be clear from the description following.

In the method of the invention, the liquid/solids reaction mixture is circulated around a loop containing a gas-transfer column. There can be one or more loops, depending on what is required, each loop containing a gas-transfer column. Normally, the mixture will be pumped around a loop in order to achieve (through one or more nozzles) the high velocity necessary to generate the foam in the column.

In the method of the invention, the downflow configuration column (or other vessel) which forms an integral part of the pumped loop is dimensioned so that at least the liquid and solids in the slurry are accelerated, for example through a nozzle or set of nozzles in parallel, the acceleration and velocity being used to shear up gas into bubbles which are concentrated into a downflowing gas-liquid bubble phase beneath the nozzle zone.

This use of hydraulic energy and turbulence, together with the concentration of bubbles within a column, provides a high interfacial area and good mass transfer coefficient for absorption of the gas into solution. The area ratio of the inlet nozzle(s) (where present) to the body of the column should be in the region of 1 to 10, and the velocity in the main body of the column should be in the region of 0.1 to 0.35 meters per second.

The liquid flow is preferably induced by an axial flow propeller pump or an Archimedian screw pump or other type of pump, integral or separate from the column, with or without a downstream nozzle zone to promote further turbulence.

The gas can be introduced into the vessel either in the neck of the vessel or beneath the nozzle(s) or in an external pump situation above the inlet nozzle(s), for example at a ratio of 0.01 to 1 volume of gas to volume of liquid flowing.

An extended pipeline loop or other arrangement can advantageously be provided-such that the hydrostatic pressure at the point of introduction of air or gas is less than the atmospheric pressure, thereby aspirating the air or gas without recourse to a compressor. The point of introduction for gas may be above (which is preferred for mass transfer) or below the orifice plate, provided that the hydrostatic pressure is below that of the ambient air or gas and that the area of pipe for gas introduction is relatively small compared with the area of the liquid pipeline at this point, i.e. not greater than ¼ of the area. On a simple volumetric ratio basis, up to ⅛ of the volumetric flow rate of liquid may be aspirated by this method.

In the method of the invention, there can be but a single micro-organism in the reaction mixture. More usually, however, there will be more than one type of micro-organism present and a mixed culture is formed, in which one micro-organism may predominate.

In pumped loop configurations, the use of a downflow gas-transfer column and relatively high turbulence and bubble density enables the bioreaction to proceed at dissolved oxygen levels as low as 0.5 to 0.6 mg/l. In general the experience in the industry is that at least 2 to 2.5 mg/l is necessary for bioreaction to proceed, and that oxygen uptake rates fall off below this level. Liu et al (Oxygen Transfer to Thiobacillus Cultures, International Bio-Hydrometallurgy Symposium, Warrick, 1987) teach that below 1 mg/l mass transfer is limiting. We believe this is due to the larger boundary layer and diffusional resistance through clumps of material that inhibits oxygen transfer in conventional systems. The benefit of being able, in accordance with the present invention, to operate at a lower overall dissolved oxygen concentration in the region of 0.5 to 0.6 mg/l is that the driving force through the pumped loop arrangement can be higher viz. 0.6 mg/l at the entry to the column and say 10 mg/l at the discharge. Thus, the driving force over the column can be some 25 to 30 percent higher than that obtainable for a mixed tank dissolved oxygen concentration of 2 to 2.5 mg/l. The amount of oxygen transferred is the product of this concentration difference times the volumetric flow rate through the column. This near-saturated liquor is then returned to the tank and rapidly mixed with the bulk contents without wastage of the dissolved oxygen. A key feature of the downflow method of contacting is that the hydrostatic head can be used to advantage, increasing the driving force for dissolution of oxygen with depth down the column.

Among the many bioreaction processes in which the present Invention can be used, one of the most important is bioleaching. Among such processes are those where the ore is sulfide containing such as iron pyrite, arseno-pyrite or another combined sulfide, and the aim is to recover or liberate gold, silver or platinum group metals, copper, nickel, cobalt, manganese, iron, zinc or lead, using a bacterium such as, for example, *Thiobacillus ferro-oxidans*. Another important area of application is the use of such bacteria for desulfurizing coal where the fuel source of the bacteria is the sulfur and no significant metals are present. We have found that in bioleaching processes, the bioleaching performance and oxygen uptake are clearly enhanced due to the high turbulence obtained in the column. The ability to work with high turbulence and shear conditions is contrary to the general teaching in the literature. There has been significant questioning of the ability of the bacteria to survive high shear conditions and potential attrition with high pulp density slurries. We have found that, at high pump density (30% w/w) and at relatively high shear, cell disruption does not appear to be a problem. On the contrary, we believe that the limitation to mass transfer that occurs in other systems is avoided, agglomerates and the clumping behavior of particles cannot occur in the column. This mechanism leads to a higher specific surface area, faster reaction rates and avoidance of obscuration of the surface by by-products, e.g. sulfur. A natural corollary of this is that the viscosity of the system appears to be lessened and the stickiness and gelatinous nature of the pulp is not apparent in the column. This has the important effect of reducing the overall power requirements, and the fouling and potential of solids buildup on surfaces, which is often reported in the literature. Care must still be taken in the design of the tank system to insure that the solids are homogeneously suspended. However, this is greatly assisted by virtue of the relatively high flow around the pumped loop.

Another effect of using this type of system is that for high pulp density slurries, in the region of 30 percent, oxygen from air may be utilised with an efficiency in the region of 40 to 70 percent during passage through the column when compared with sparged tanks operating at similar hydrostatic head and pulp density where the utilisation efficiency may be only 2 to 20 percent. Higher efficiencies are obtainable on an overall basis when the bubbles are released into the main tank since they enter as a swarm of small, relatively uniform size bubbles at the base of the tank and still have some capacity to transfer any residual oxygen on their passage to the surface. Furthermore, if oxygen rather than air is employed, the efficiency of utilisation can be considerably higher at 75 to 100 percent, the latter being achievable for lower operating column velocities within the specified range.

The loop (or loops) employed in the method of the present invention can be located within or outside the reaction vessel containing the biomass. Where an external column and pumped loop are employed, maintenance is improved significantly since there is no distributor system to foul and no need for personnel to enter the tank to carry out maintenance. This is a particular benefit of the system because maintenance personnel require breathing apparatus and settled solids are not easily handled or pumped. Such bioreactions generally lead to the formation of gelatinous products which can foul surfaces and stick to distributors, reducing their performance or completely block them in relatively short periods of time. By contrast, the reactor loop situation has sufficient flow rate and large clearances leading to much less maintenance requirement.

Another important advantage provided by the use of a pumped loop is the facility of injecting nutrients and/or inoculant directly into the column. This is ideal as it is a region of high oxygen uptake and mixing, and both nutrients and inoculant may be rapidly mixed and distributed in the main tank through this method. Another consideration here is often bacteria, especially *Thiobacillus ferro-oxidans*, require carbon dioxide for cellular growth, and again $CO_2$ is advantageously introduced at this point.

Since a relatively high quantity of liquid passes around the pumped loop configuration, natural stirring of the tank can be achieved by appropriate direction of the returned liquor. This minimises the power requirements for conventional stirrers or can indeed replace them in their entirety.

In one embodiment of the invention (illustrated and described hereafter in FIGS. 4 and 5 of the accompanying drawings), the column is constituted by an annular chamber formed around the main reaction vessel. This arrangement can provide certain economies in capital plant expenditure. The reaction mixture from the main vessel is flowed in a loop, i.e. into the top of the annular chamber and therein oxygenated as in a column, and then from the base of the annular chamber back into the reaction vessel.

Overall the method of the invention results in reduction of energy for compression of air, for stirring of liquid and for transfer of necessary oxygen and carbon dioxide into the biomass. Furthermore, heat transfer is improved due to the higher velocities within the system, and the column itself may be used as an external source of heat loss directly from its shell or by provision of coils or cooling jackets. Bacteria such as *Thiobacillus ferro-oxidans* operate optimally at temperatures in the region of 35 to 38° C. where the rates of bioleaching are maximised. The ability to closely control the temperature can optimise this reaction rate. Another consideration in the controllability of this type of process is that each pumped loop arrangement, of which there may be a number on each tank, can be specifically tuned to the requirements of each tank in a chain of tank reactors. Thus, adjustments can easily be made to oxygen uptake, carbon dioxide supply, inoculant injection, nutrient addition, etc. to satisfy the changing requirements of the process and meet the altered conditions of ionic strength ($Fe^{2+}/Fe^{3+}$ level), viscosity, $k_La$ value etc. as the reaction proceeds. Furthermore, high turndown is possible, and startup and shutdown of the overall system is simplified.

The method of the invention can be applied to a variety of situations and different pulp densities. Provided the slurry can be pumped satisfactorily, the mechanism can be used for efficient introduction of air/oxygen or other gases. This is not the case with stirred tank reactors where energy requirements increase dramatically with solids pulp density and lead to a significant reduction in $k_La$ and oxygen transfer rates.

Projections using the equations developed by Liu et al (supra) indicate that for similar power inputs to our experimental conditions, $k_La$ values are particularly low, in the region of 0.002 sec$^{-1}$. By contrast, we have measured $k_La$ values some 50 to 100 fold times these values in the region of 0.1 to 0.3 sec$^{-1}$ when operating at 30% pulp density. The ability to transfer oxygen into solution and thence to the solids surfaces and the bacteria is directly proportional to this volumetric mass transfer $k_La$ value.

Because the column concept provides a fully flooded, downflow bubbling mode of operation and minimised use of air, the gases (nitrogen) vented from the tank are minimised, and foaming and froth formation is avoided or minimised together with the exhaust gas handling requirement on an overall plant.

A number of processes are reported in the prior art for using bacteria for leaching. *Thiobacillus ferro-oxidans* has been applied successfully on sulfides of copper and uranium and operates ideally at pH 1 to 2 at 35° C. and at relatively low dissolved oxygen concentrations of around 1 to 2 mg/l. It also requires $CO_2$ for propagation of the cellular carbon. The mechanism is one of direct oxidation with *Thiobacillus ferro-oxidans* generating ferric sulfate solution at the low pH. The uranium is solubilized by the ferric ions which are generated as a by-product from pyrite oxidation. The mechanism is similar for chalcopyrite.

Nickel, molybdenum, and cobalt, present as their sulfides can also be effectively solubilized by these bacteria by such a direct oxidation reaction route. On the other hand, gold, silver and platinum group metals, which are often encapsulated in a pyritic lattice, for example, in low grade or so-called "refractory ores", can be recovered indirectly by attacking the pyritic lattice with such a bacteria. Only partial leaching of this pyrite can result in the liberation of the precious metal for subsequent recovery by conventional techniques, e.g. cyanide leaching.

In the case of desulfurization of coal, *Thiobacillus ferro-oxidans* has been found to be particularly successful in treating the pyritic sulfide or inorganic sulfide component in the coal, and other techniques are being developed for treatment of the organic sulfur content.

In addition to *Thiobacillus ferro-oxidans*, other bacteria may be used for such mineral bioleaching operations. One, in particular, is Sulfolobus (such as *Sulfolobus acidocaldarius*) which is thermophilic and operates at temperatures in the region of 65 to 70° C.

For coal desulfurization, Sulfolobus is a potentially valuable strain of bacteria, since working at higher temperatures, it might be expected to operate at faster rates. For this purpose, the pumped loop arrangement of the present invention, operated in conjunction with a relatively deep tank for higher hydrostatic head, is particularly advantageous with air or oxygen. For such a system at 70° C., using atmospheric air and a 20 m deep tank, in excess of 60 percent of the oxygen can be utilized up to 90 to 95 percent of the pyritic sulfur removed in a five to seven day period. Similar results apply for these bacteria on refractory gold ores where over 90% gold recovery can be achieved by operation with a pumped loop aeration of the invention system in as little as two to three days.

In the bioleaching of low-grade refractory gold ores containing 2 percent pyritic sulfur, over 90 percent recovery of gold can be achieved (at 0.18 troy ounces Au/tonne) by oxidizing only 40 to 50 percent of the total sulfur. Using oxygen and *Thiobacillus ferro-oxidans* with 30 percent solids density slurry, this can be achieved in three stages of reaction over a total period of 40 hours. Oxygen utilization is in excess of 90 percent using two pumped loops per tank each at 1.5m3/s and discharging into the base of 20 m deep tanks. Each column is 3 m diameter and 3 m high and can transfer up to 50 mg/l oxygen differential across it. Operating power for oxygenation is less than 350 kW for the total installation.

Other applications of the system of the invention include biodegradation of hazardous wastes and activated sludge or effluent treatment where pulp densities are in the region of 5% w/w and mixed aerobic bacteria are present. Such processes can benefit by the efficiency of transfer of oxygen or the lower power requirements.

Also, the pumped loop bioreactor arrangement of the present invention can be employed in the fermentation field. Fermentation of glucose using *Xanthamonas campestris* microbes to yield xanthum gum, a polysaccharide, is one such fermentation. Due to the non-Newtonian behaviour of the broth, it is difficult to transfer oxygen to the bioculture without considerable power inputs when using a sparged, stirred tank fermentor. For viscous cultures such as this, high shear is essential for efficient transfer of the oxygen. This feature can be provided most satisfactorily by the pumped loop arrangement of the invention. Recirculation rate can be selected to ensure the tank contents are well mixed and oxygen or air applied to match the biological uptake rate.

In order that the invention may be more fully understood, reference is made to the accompanying drawings in which:

FIG. 6 is a schematic vertical sectional view of another tank/column arrangement according to the present invention;

FIG. 7 is a simplified top plan view of the column of FIG. 6; and

FIG. 8 is a schematic vertical sectional view of a tank/column arrangement similar to that in FIG. 6.

The engineering problems associated with providing a three-phase system (gas, liquid and solid) for handling a mineral slurry are significant. Conventional chemical engineering approaches such as packed towers or columns or spray contactors in addition to the stirred tank reactor approach mentioned earlier, suffer severe shortcomings due to blockage, plugging, or general loss of performance in the presence of high solids loadings. The present application, however, describes a method for such three-phase contacting which is applied to bioreactor design.

Figure 1A:
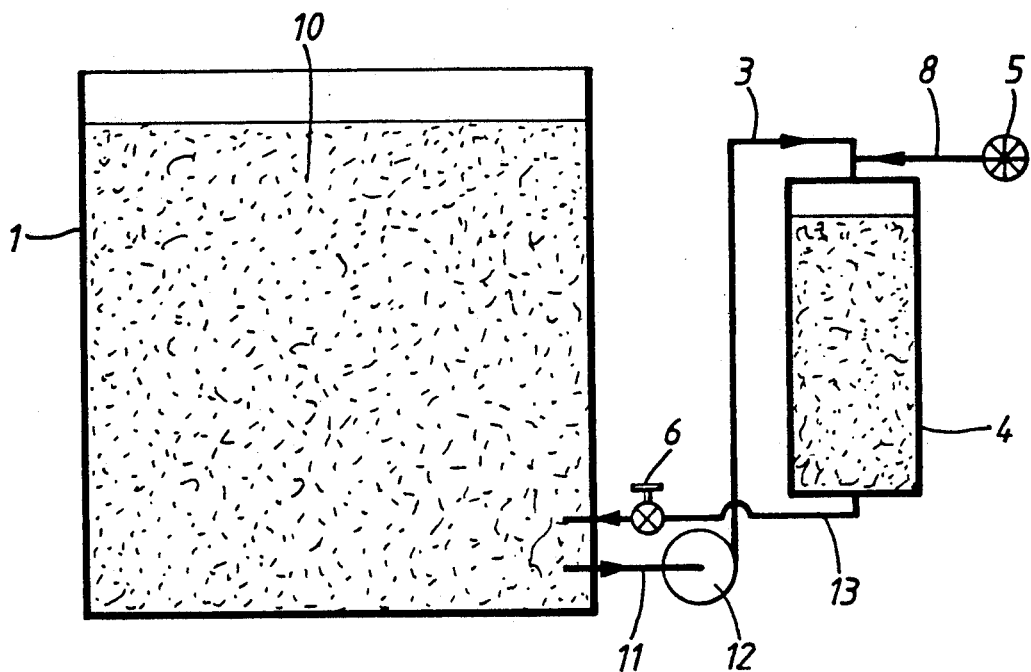
FIG. 1A is a schematic vertical sectional view of one arrangement for carrying out the method of the invention, with an external column.

Referring to FIG. 1A of the drawings, there is shown a main reaction vessel 1 which contains the liquid/solids reaction mixture 10. At or near the bottom of the tank is an outlet pipe 11 connecting to a pump 12. From pump 12, pipe 3 connects to the top of a column 4. An air supply is provided along line 8 from compressor 5 to mix with the liquid/solids mixture prior to entry into the column 4. From the bottom of the column, the treated reaction mixture is returned to vessel 1 through pipeline 13 which includes a valve 6.

Figure 1B:
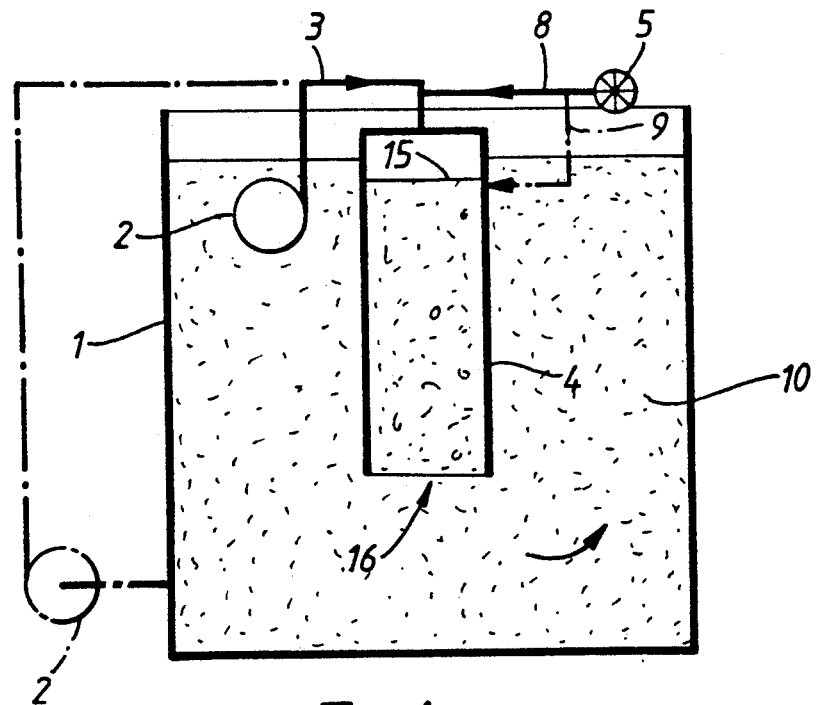
FIG. 1B is similar to FIG. 1A but with an internal column.

The arrangement shown in FIG. 1B is generally similar, and like numerals indicate like parts to FIG. 1A. However, in FIG. 1B, the column 4 is inside the vessel 1. Pump 2 can be inside vessel 1 or (as shown in phantom) outside vessel 1. In both cases, the pump draws liquid/solids from tank 1 and delivers it via pipeline 3 to the top of column 4. Two alternative gas supply arrangements are shown in FIG. 1B. One is the same as in FIG. 1A, i.e. supply of gas to the liquid/solids before entry into the column, and the other (in phantom) shows supply of gas via line 9 into the column at about the top level 15 of the liquid/solids contents in the column. In FIG. 1B, the low end 16 of the column 4 is open.

In both FIGURES, the loop is constituted by the flow path from vessel 1 via the pump 2 to the top of column 4, down through the column and out into the vessel 1.

Within the column 4 (in both FIGS. 1A and 1B), the hydraulic energy of the flowing fluid is preferably utilized through a nozzle arrangement (not shown in FIGS. 1A and 1B) operated in downflow configuration for inducing turbulence and shearing up gas into bubbles. By appropriate selection of the nozzle(s) geometry in relation to the main body of the column, improved gas-liquid mass transfer coefficients and substantial interfacial areas can be achieved for less power than in a stirred tank reactor or column using a high pressure drop diffuser. The column 4 can be operated under a wide range of pressures, from atmospheric to above, using either the hydrostatic head availability in the tank and/or the resistance to backflow generated by a pressure reducing valve. Significant amounts of gas (air/oxygen) can be dissolved, even in the presence of solids. Solids loadings in the region of 1% to 50% w/w have been evaluated and are viable.

The liquid is accelerated through the entrance passageway or nozzle(s) which is preferably so configured to provide fairly precise relationships between the liquid velocity in the column entry zone and the subsequent velocity in the body of the column. Turbulence is generated providing rapid shear of bubbles, and the provision of interfacial area for mass transfer of the gas into solution. This three-phase mixture of back mixing turbulent bubbles can be operated in such a way that the bubbling phase extends down the vessel in proportion to the amount of air or gas to liquid ratio. The air or gas can be supplied from a higher pressure source, such as a compressor 5 as shown delivering air into the nozzle or influent pipeline region. The column itself may be operated at pressures significantly in excess of atmospheric depending on the relative positioning of the column, vis-a-vis the tank, or its position within the tank. Alternatively, the pressure within the column can be increased above atmospheric pressure and/or the hydrostatic pressure of the tank by virtue of a special restriction orifice or valve 6 (FIG. 1A), on the discharge of the vessel. Because the contacting method develops high interfacial areas between the gas and liquid, rapid mass transfer of gas (oxygen) into solution, and equilibrium or near equilibrium conditions, are achieved in a relatively short length of column. Different methods are possible for promoting the flow of the slurry and the introduction of the gas, but the principal energy consideration is that significant quantities of gas can be dissolved for relatively low hydraulic pumping and negligible gas compression requirements. An axial flow propeller pump 2 provides a convenient, high-efficiency method of providing the hydraulic head rise necessary to overcome the nozzle(s) pressure loss and the overall system frictional resistance, yet is capable of handling high solids loading. Yet another method of achieving the high flow, but relatively low hydraulic head, with efficiency is the Archimedes type screw pump.

A preferred feature of the design is that the ratio of the velocity through the nozzle(s) to the velocity in the body of the column downstream should be high, e.g. of the order of 10:1. The velocity in the body of the column should generally be in the region of 0.1 to 0.35 meters per second for optimal contacting. The main body of the column should preferably be parallel sided, although a very slight expansion or contraction of the flow area is not deleterious within the above velocity and expansion ratios. The body of the column would not typically he less than one to two meters in most applications, and in certain instances greater column lengths will provide better gas utilization and approach to equilibrium.

The discharge through the pipeline or base of the column may be so designed that the velocity of discharge can be used for mixing the total contents of the tank or bioreactor into which it discharges. This pumped loop may therefore be used as a means of keeping gas/liquid concentrations even and mixed throughout the bioreactor (tank) as well as particulates, i.e. solids, in suspension. In some bioreactors, the gas absorbed may be air or oxygen or carbon dioxide or nitrogen alone or in a combination, depending on the requirements of the appropriate biomass.

Typical gas/liquid ratios depend on the solids concentration and the proportion of dissolved gas required. Typical gas-to-liquid ratios would be in the region of, for example, 0.01:1.0 volumes of gas per volume of flowing liquid. If it is desired to provide oxygen directly to a biomass, this may be achieved by supplying bulk oxygen, in which case substantially all of the gas can be taken into solution in the column or gas contacting vessel. Where the oxygen is supplied from an air source, not all the gas can be taken into solution and bubbles, principally of nitrogen with some unabsorbed oxygen, will exit the column into the tank or bioreactor.

Figures 2A, 2B:
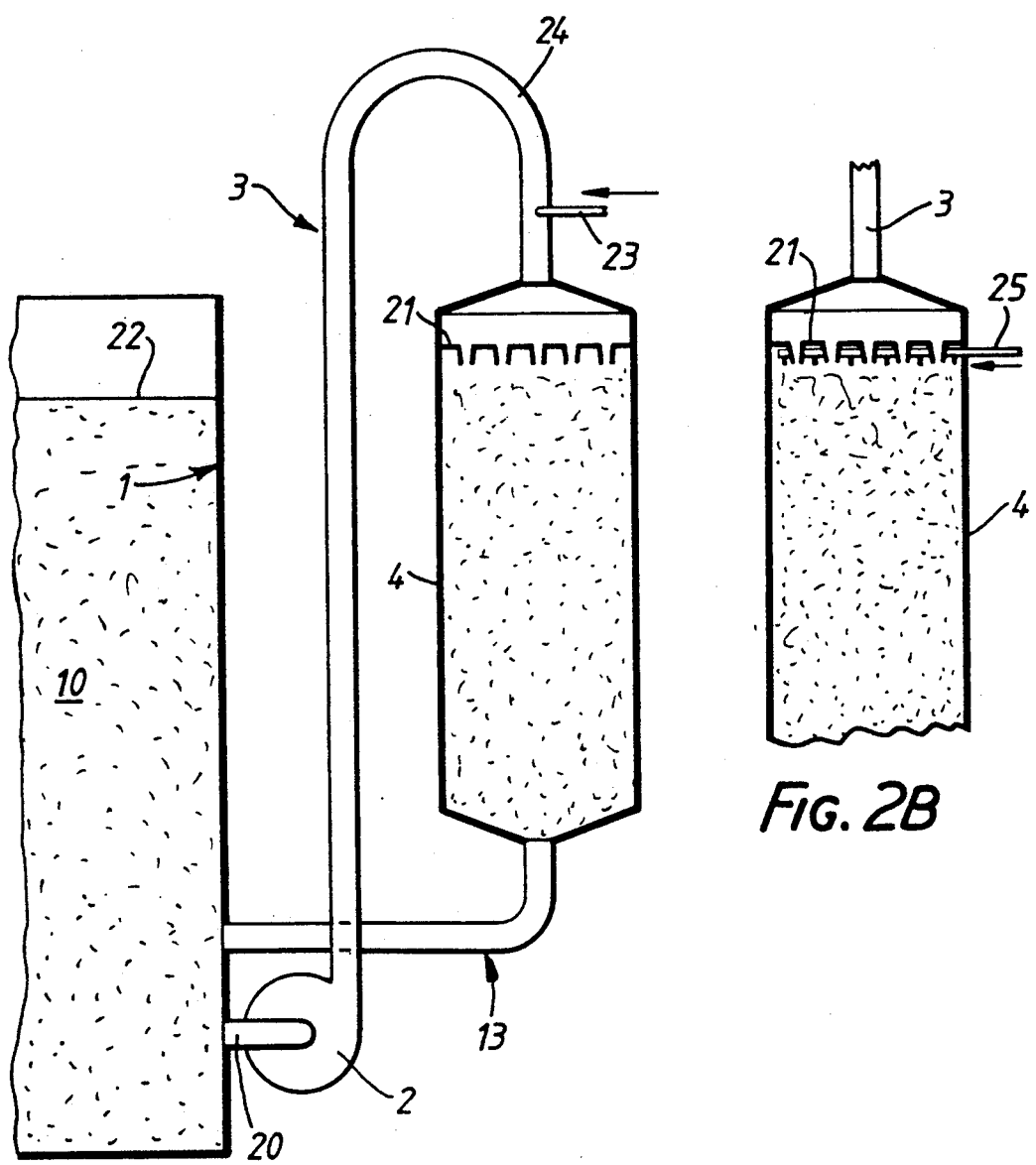
FIGS. 2A and 2B show the column in schematic vertical section with alternative air entries.

It has been found that it is not always necessary to use a compressor to introduce the gas into the liquid/ solids mixture. FIGS. 2A and 2B illustrate embodiments where no compressor is used. FIG. 2A shows part of main reaction vessel 1, with an outlet 20 connected to pump 2. From pump 2, line 3 connects in a looped region 24 to the top of column 4. The column is shown in slightly more detail than in FIGS. 1A and 1B, and includes a nozzle plate 21. From the bottom of column 4 pipeline 13 returns to vessel 1. The level 22 of liquid/solids 10 in vessel 1 is also shown.

In the arrangement of FIG. 2A, atmospheric air is aspirated via pipe 23. Pipe 23 has substantially less than ¼ of the cross-sectional area of the main pipe loop 24 It has been found that up to ⅛ of the total volumetric flow rate of liquid can be induced in the form of atmospheric air when operating the system at close to atmospheric pressure. For the above to be effective, it is important that the pressure loss across the nozzle bank 21, together with the system frictional resistance, does not exceed the hydrostatic head equivalent to the position of gas entry above the tank level.

FIG. 2B is the same as FIG. 2A except that, in FIG. 2B, pipe 23 is omitted and the air admission is via pipe 25 into the column at the nozzle level therein. This will work provided the residual frictional resistance in the pipeline 25 and column do not exceed the hydrostatic head for the introduction of gas at this point. It is important, however, that the gas pipe 25 for the introduction of air or gas by this aspiration method should be small relative to the body of fluid at the point of introduction so that bubbling rather than gas pockets can be generated. The production of a gas pocket will lead to a significantly increased energy requirement for the pumping system and a dramatic loss of interfacial area.

Figure 3:
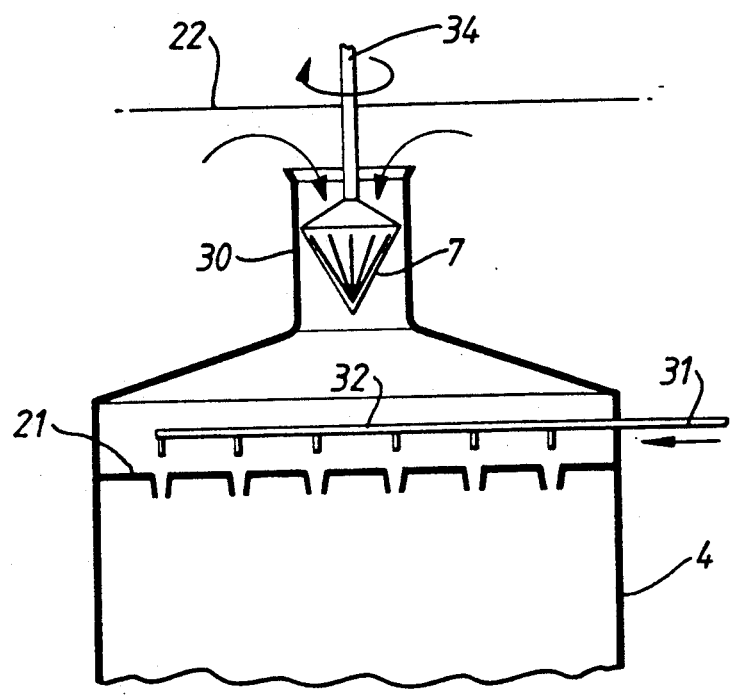
FIG. 3 is a vertical section of the top of the column also showing an optional pump arrangement.

FIG. 3 illustrate an alternative to the positioning of pump 2 in FIGS. 1 and 2. Thus, FIG. 3 shows the top of column 4 with nozzle plate 21 disposed in the column. The column 4 has a neck 30 through which the liquid/solids feeds into the column. In this embodiment, air inlet 31 connects to a gas distribution pipe 32 disposed across the column above (or below) the nozzles. As drawn, the column is within the main reaction vessel (as in FIG. 1B) and the liquid/solids level 22 in the tank is illustrated.

Disposed in neck 30 is an axial flow impeller 7 driven by shaft 34. This is instead of pump 2 (FIG. 1B).

This arrangement merely illustrates one possible alternative; there are others for promoting fluid flow around the loop.

Figure 4:
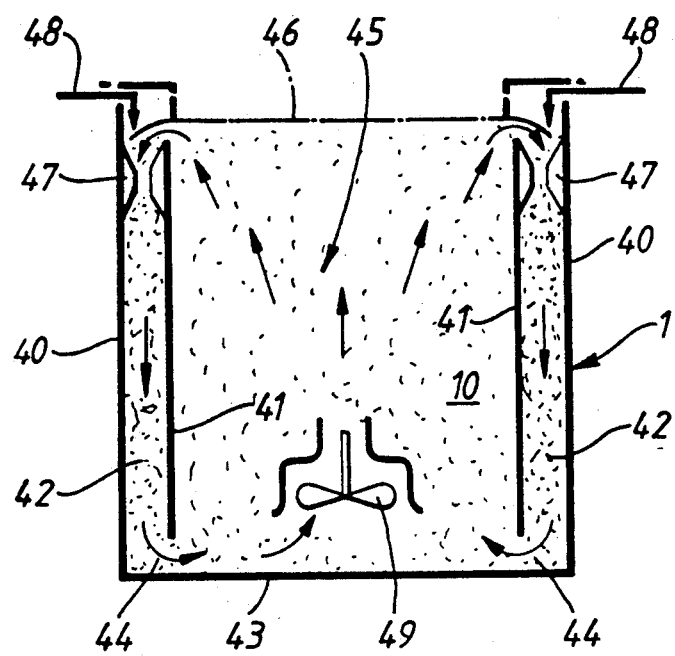
FIGS. 4 and 5 are schematic vertical sectional views of alternative tank/column arrangements for carrying out the method of the invention.
Figure 5:
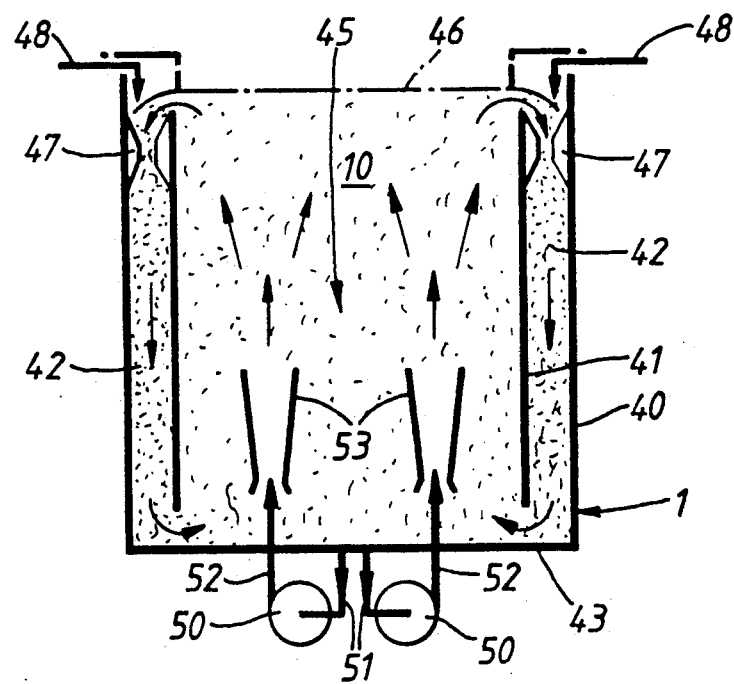

In many biochemical reactions involving gas/liquid and solids, it is necessary positively to control the temperature of the reaction mixture, and often this is difficult to achieve on a commercial scale. In accordance with a preferred feature of the present invention, however, the flow conditions in the loop offer excellent heat transfer conditions, and by the provision of heat transfer means (e.g. external cooling jackets or internal heat exchanger, tubes, coils or the like) in the loop, temperature can be readily controlled either by adding or removing heat. FIGS. 4 and 5, in which like numerals indicate like parts, illustrate the use of an annular column. Referring to FIG. 4, the main reaction vessel 1 contains the liquid/solids reaction mixture 10. Spaced internally of the outer wall 40 of vessel 1 is an internal wall 41, the space between the walls 40 and 41 defining a chamber 42. Where tank 1 is circular, the chamber 42 is annular. The internal wall 41 terminates above the bottom 43 of vessel 1, to provide an outlet 44 from chamber 42 into the central region 45 of vessel 1. The wall 41 terminates below the normal liquid/solids surface level 46 in vessel 1, to allow the reaction mixture to pass into the top of chamber 42. Air (or other gas) is supplied via line 48 to the top of chamber 42 (by means previously described) and means are provided in chamber 42 to accelerate the reaction mixture downwards in the chamber 42. As illustrated, these means are restrictions or nozzles 47. In the central region 45 of tank 1 is a high volume pump or stirrer 49.

In operation, the pump 49 drives the liquid/solids reaction mixture upwardly in region 45 and into the top of the chamber 42 wherein it is accelerated downwardly and oxygenated (or contacted with another gas). The conditions in the chamber 42 are essentially the same as in the columns previously described, and thus the chamber 42 is considered to be a column. The treated reaction mixture flows radially inwardly through outlet 44 back into the central region 45 of vessel 1. The space between the inner and outer walls (41,40), i.e. the width of the chamber 42, is chosen so that the upward rise velocity for a swarm of bubbles is exceeded by the downward liquid velocity and is thus principally related to the pumping rate selected to achieve the mass transfer duty.

FIG. 5 is the same as FIG. 4 except that external pumps 50 are used with venturi augmenters to move higher volumes of liquid. Each pump 50 draws mixture from the bottom 43 of vessel 1 via pipe 51, and returns it via pipe 52 to venturi augmenters 53 within region 45 of vessel 1. Although the pumps 50 as illustrated are outside the vessel 1, they may in an alternative arrangement be within the vessel 1.

FIG. 6 shows a bioreaction vessel 1 (only part shown) containing liquid/solids reaction mixture 10. The column 4 is located outside vessel 1. Liquid/solids mixture 10 is withdrawn from the upper part of vessel 1 through an outlet 60 via a pump 61 and delivered through pipe 62 tangentially into the top of column 4. A small bleed of higher velocity flow mixture is passed through bleed pipe 63 to enter vertically downwardly into the top column 4, on the axis thereof. Bleed pipe 63 can be closed by a valve 64. Two oxygen (or other gas) introduction means are shown. The first is a tee or branch 65 in line 62 and the second a tee or branch 66 (with a valve 67) in bleed pipe 63.

The upper part 68 of column 4 is of smaller diameter than the lower part 69. At the bottom of lower part 69 is an outlet pipe 70 for returning the treated mixture to the main reaction vessel 1. The lower part 69 of the column 4 contains oxygen-saturated liquor, and upon its return to vessel 1 the dissolved oxygen is consumed directly from solution by the biomass present in suspension and on the solids.

The introduction of liquid/solids mixture tangentially into the column 4 imparts a swirling motion to the column contents at least in the upper part 68 thereof. A dense bubble phase or foam is established in the column dissolving oxygen directly into the liquid. Because of the swirling motion, bubble coalescence occurs. The oxygen is therefore used efficiently and the liquor leaving the column 4 is saturated with oxygen.

FIG. 7 is a simplified top plan view of the column (omitting most of pipe 63). Like numerals to FIG. 6 indicate like parts.

The arrangement of FIG. 6 is especially useful when oxygen is used. When air is used instead, the liquid being circulated around the loop (vessel 1, pipes 60, 62, 63, column 4, outlet 70) becomes saturated with nitrogen. In this case, nitrogen bubbles leave the bottom of the column and are swept into vessel 1. In these circumstances, certain modifications can advantageously be made in the arrangement of FIG. 6. Thus, the increased diameter of column lower part 69 over upper part 68, which serves to prevent bubbles leaving column 4 in the arrangement of FIG. 6, is no longer of benefit and a parallel sided column 80 can be used instead (FIG. 8). Further, in vessel 1, a baffle 81 is preferably provided to prevent unwanted nitrogen bubbles from circulating.

Also, air is preferably supplied into bleed pipe 63 along line 66 from a compressor 82. These changes are shown in FIG. 8, where like numerals to FIG. 6 illustrate like parts.

In order that the invention may be more fully understood, the following Example is given by way of illustration only.

EXAMPLE

An example of a process of the present invention is here compared with a process in a conventional design of bioreactor, for a mineral leaching operation.

The conventional bioreactor comprises a tank 10 meters in diameter, 12.5 meters operating depth, and contains a slurry of 25% w/w solids content. The solids contain 1.5% sulfide ore as pyrite ($FeS_2$) which itself has an entrapped gold content. The aim is to digest the sulfide ore in a series of stages to liberate the gold using a bacterium, *Thiobacillus ferro-oxidans*, according to the overall reaction:

$$4FeS_2 + 2H_2O + 15O_2 \rightarrow 2Fe_2(SO_4)_3 + 2H_2SO_4$$

In the first tank or bioreactor of a series to convert 25% of the sulfide, approximately 160 kg/h of oxygen must be absorbed into solution. Air must be supplied at the rate of 3,400 kg/h, i.e. roughly five times the theoretical oxygen requirement, to achieve this duty. This corresponds to only 20% efficiency of oxygen transfer. Furthermore, the compression energy required for the air to introduce the gas at a back pressure equivalent to 12.5 m of slurry is 130 kW.

In addition, a further 15 kW are required to maintain adequate mixing in the tank. By contrast, according to the present invention, the same amount of oxygen may be transferred in a pumped loop carrying 4.4 $m^3$/s of slurry, aspirating 1,380 kg/h of air for a total power requirement of only 89 kW. Furthermore, the tank itself can be considered adequately mixed and the solids suspended due to this return flow. The columns in the pumped loops comprise vessels of dimensions 2 m diameter by 2.5 m long and incorporate an orifice plate 8, as shown in FIG. 3, having provision for a number of nozzles each operated at a design flow velocity of 3.5 m/s. The velocity in the body of each column is 0.35 m/s. At the operating pressure, a change in dissolved oxygen from inlet to outlet of 9 to 10 ppm (mg/l) can be achieved.

For processing 20 tonnes of refractory gold ore per hour (dry solids basis), four tanks of identical size are used, each nominally 1,000 m3. Each tank provides 15 hours of residence time, and therefore the total reaction residence time is 60 hours. As the reaction proceeds, the iron concentration n solution increases according to the typical 'S' curve developed from laboratory batch tests. Each stage of the reaction sequence at full scale has a different dissolved iron concentration design point ranging from approximately 1.3 to 5.0 g/l. Overall about 90 percent of the pyritic iron (combined as sulfide) is converted through to ferric sulfate, and the gold recovery in the subsequent cyanide leaching is in the 95 to 100 percent range.

In order to maintain optimum temperature, it is necessary to have sufficient heat exchange surface area and coolant availability. Heat generation for the above situation is theoretically 6 GJ/h (although not all of this is manifest in practice) which cannot be dissipated naturally. Heat exchange directly from the pumped loops to water jackets is an efficient solution to the problem.

We claim:

1. A method of effecting a bioreaction which comprises introducing a gas into a mixture comprising a continuous liquid phase material and a solid biomass dispersed therein, the mixture containing a microorganism to enable the bioreaction to proceed, which comprises confining the mixture in a reaction vessel and circulating the mixture around a loop, the loop including a column in which gas transfer is effected, at least the liquid being introduced into the top of the column in the form of at least one stream, the velocity of which stream(s) is sufficient to generate and maintain, at least in an upper region of the column, a substantially continuous foam formed of close-packed bubbles of the gas in the liquid extending across the entire cross-section of the column, driven to violent agitation and backmixing by the incoming stream(s) of liquid, and of relatively uniform bubble size, the velocity of the inlet stream(s) of liquid and the rate of introduction of the gas being sufficient to prevent gas from accumulating at the top of the column.

2. A method according to claim 1, wherein the mass of liquids/solids and gas in the column is rotated in the column substantially around the central vertical axis of the column with a superimposed vertical circulating movement, the net flow of liquids and solids being downward through the column.

3. A method according to claim 1 wherein the solids comprise a sulfide-containing ore which includes one or more of the metals Au, Ag, As, Pt, Pd, Rh, Co, Cu, Fe, Mn, Ni, Zn or Pb, and wherein the method is operated to recover or liberate one or more of said metals.

4. A method according to claim 3, wherein the mixture contains the micro-organism *Thiobacillus ferro-oxidans* and, optionally, one or more other micro-organisms in a mixed culture.

5. A method according to claim 1, wherein the solids comprise a carbonaceous material such as coal, and wherein the sulfur content of the said material is reduced by the method.

6. A method according to claim 3, wherein the ore is iron pyrite, arseno-pyrite or another combined sulfide.

7. A method according to claim 1, wherein the gas comprises oxygen.

8. A method according to claim 7, wherein the dissolved oxygen level in the reaction vessel can be as low as 0.5 to 0.6 mg/l.

9. A method according to claim 8, wherein the driving force through the loop is about 0.6 mg/l at the entry to the column and about 10 mg/l at discharge from the column.

10. A method according to claim 7, wherein the liquid discharging from the column is at least near-saturated with dissolved oxygen.

11. A method according to claim 10 wherein the liquid discharging from the column is supersaturated with dissolved oxygen relative to the tank contents by operation at a higher pressure in the column than in the tank.

12. A method according to claim 1, wherein the liquid/solids mixture has a pulp density of from 0.1 to 50%(w/w) and wherein the gas comprises air.

13. A method according to claim 12 wherein the liquid/solids mixture has a pulp density in the region of 30% w/w and wherein the said gas is substantially pure oxygen or oxygen-enriched air.

14. A method according to claim 1, wherein the nutrients and/or inoculant are added to the mixture by introduction directly into the column.

15. A method according to claim 14, wherein the biomass requires carbon dioxide for respiration and carbon dioxide is introduced directly into the column.

16. A method according to claim 1, wherein the mixture is pumped around the loop, and the circulation is used to stir the mixture in the vessel.

17. A method according to claim 1, wherein the gas is introduced into the liquid/solids mixture at a point where the hydrostatic pressure is less than atmospheric.

18. A method according to claim 1, wherein the mixture contains the micro-organism Sulfolobus.

19. A method according to claim 18, wherein the mixture contains the micro-organism *Sulfolobus acidocaldarius.*

20. A method according to claim 1, wherein the mixture contains the micro-organism *Xanthamonas campestris.*

* * * * *